United States Patent [19]
Riggi et al.

[11] Patent Number: 4,524,152
[45] Date of Patent: Jun. 18, 1985

[54] 1-CYANO-3-(FLUOROALKYL)GUANIDINES FOR LOWERING BLOOD PRESSURE

[75] Inventors: Stephen J. Riggi, Fairport, N.Y.; Robert N. Haszeldine, Disley, England

[73] Assignee: Pennwalt Corporation, Philadelphia, Pa.

[21] Appl. No.: 454,759

[22] Filed: Dec. 30, 1982

[51] Int. Cl.³ .................. C07C 129/14; A61K 31/155
[52] U.S. Cl. ..................................... 514/609; 564/104
[58] Field of Search ................. 564/104; 424/304, 326

[56] References Cited

U.S. PATENT DOCUMENTS 2,455,894  12/1948  Lecher et al. ................. 564/104
2,479,498   8/1949  Lecher et al. ................. 564/104
2,539,558   1/1951  Studeny et al. ............. 564/104 X
2,897,162   7/1959  Lowe et al. .................. 564/104 X
3,308,022   3/1967  Cummings et al. ............... 424/326

Primary Examiner—Thomas A. Waltz

[57] ABSTRACT

1-Cyano-3-(fluoroalkyl)guanidines of the formula:

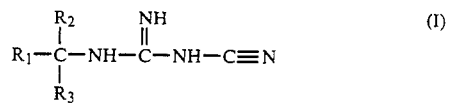

in which $R_1$, $R_2$ and $R_3$ are the same or different members of the class of hydrogen, fluorine, lower alkyl or lower alkenyl provided that at least one member is fluorine or fluoro-substituted alkyl or alkenyl. These compounds are useful for their biological properties, e.g. in treating elevated blood pressure and Parkinson's disease.

7 Claims, No Drawings

1-CYANO-3-(FLUOROALKYL)GUANIDINES FOR LOWERING BLOOD PRESSURE

SUMMARY

This invention provides 1-cyano-3-(fluoroalkyl)-guanidines of the formula:

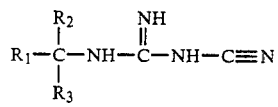
(I)

in which $R_1$, $R_2$ and $R_3$ are the same or different members of the class of hydrogen, fluorine, lower alkyl or lower alkenyl provided that at least one member is fluorine or lower fluoroalkyl. These compounds are useful for their biological properties, e.g. in treating elevated blood pressure and Parkinson's disease.

BACKGROUND OF INVENTION

Gadekar et al., [J. Med. Chem. 11, 811–814 (1968)] prepared a series of 1-cyano-3-substituted-guanidines which exhibited antihypertensive and hypotensive activities. An undesirable action frequently found with guanidine and cyanoguanidine compounds is that of ganglionic blockade and it was noted that the nature of the 3-substituent is critical for obtaining hypotensive effects without ganglionic blockade. The desirable profile appeared to be restricted to a series of 3-lower alkyl derivatives in which the carbon alpha to nitrogen is branched. Such structures as (II) are disclosed in U.S. Pat. No. 3,308,022.

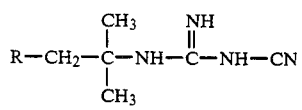
(II)

Certain of these compounds are potent hypotensive agents, and the preferred compound is guancydine (II, R=CH$_3$) which has been studied in animals and man. Guancydine has several undesirable side effects (Drugs of the Future, Vol. III, No. 4, 1978, pp. 291–294 and references therein, Martindale's The Extra Pharmacopeia, 27th Edition (1977) p.1765) including urinary retention, oedema, sinus tachycardia, weight gain, gynaecomastia and nausea. None of the disclosed compounds contain fluorine substituents. Due to the physiochemically distinct yet sterically similar characteristics of hydrogen and fluorine, fluorine substitution for hydrogen in drug moieties may alter the physical and biological properties often with enhancement of the desired activity and has resulted in the development of many new drugs. Examples of fluorinated drugs with enhanced properties are to be found in the treatment of many diseases. The following references to the Merck Index (9th Edition) are representative; triamcinolone #9279, dexamethasone #2899, fluoxymesterone #4070, flurazepam #4078, fenfluramine #3902, and 5-fluorouracil #4067. Such substitution may result in unexpected changes in potency, rate of absorption, duration of action, and the elimination of undesirable side effects.

The compounds of formula (I) possess useful pharmacological properties, e.g. they exhibit antihypertensive, vasodilator and dopaminergic activities. It will be obvious to those skilled in the art that stereoisomers, racemates and optically active forms of any of the compounds of formula I are possible and such forms are comprehended within the scope of the invention. By the terms "lower alkyl" and "lower alkenyl" as used in defining "R" groups are meant such groups containing no more than about six (6) carbon atoms. Particularly satisfactory from the point of view of antihypertensive activity is that class of compounds wherein $R_2$ and $R_3$ are methyl and $R_1$ is an alkyl group containing fluorine; and the compound of formula I wherein $R_1$ is CF$_3$CH$_2$— and $R_2$ and $R_3$ are CH$_3$ is a preferred species, exhibiting pronounced antihypertensive effect even after 24 hours as determined by its effects on the blood pressure of Spontaneously Hypertensive Rats (SHR).

The compounds of this invention are prepared by reacting an amine of formula (III) with sodium dicyanamide in an appropriate solvent (such as n-butanol) at elevated temperatures, preferably at from about 90°–120° C. for a period of from about 12 to 120 hours. The reaction proceeds according to the following equation:

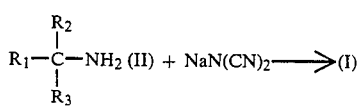

The amines of formula (III) can be prepared by a number of methods. Many suitable such amines are known in the prior art and related novel amines can be prepared by techniques completely analagous to those employed in the art. Various preparatory embodiments (wherein "X" is halogen) are illustrated diagramatically in Schemes 1–6 below.

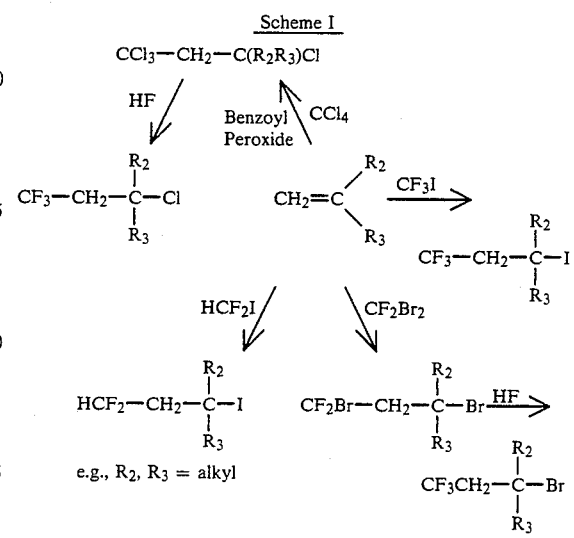

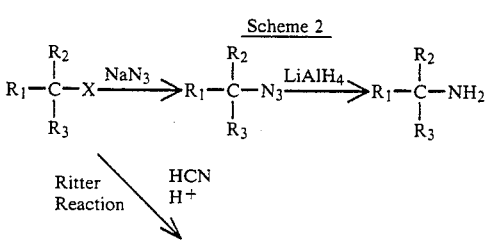

-continued
Scheme 2

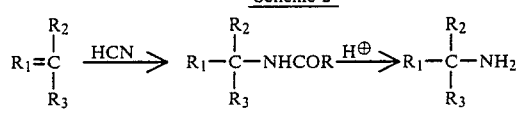

Scheme 3

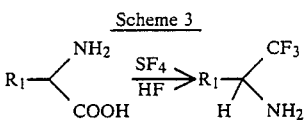

Scheme 4

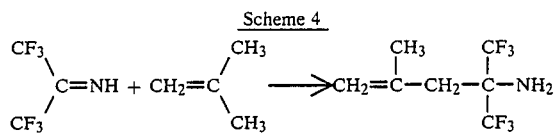

Scheme 5

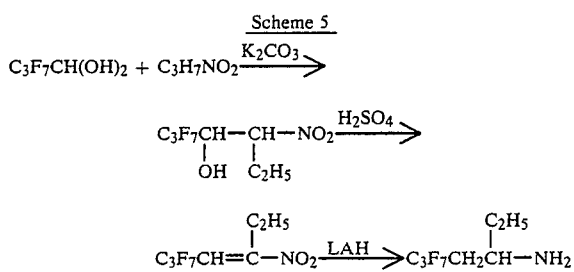

Scheme 6

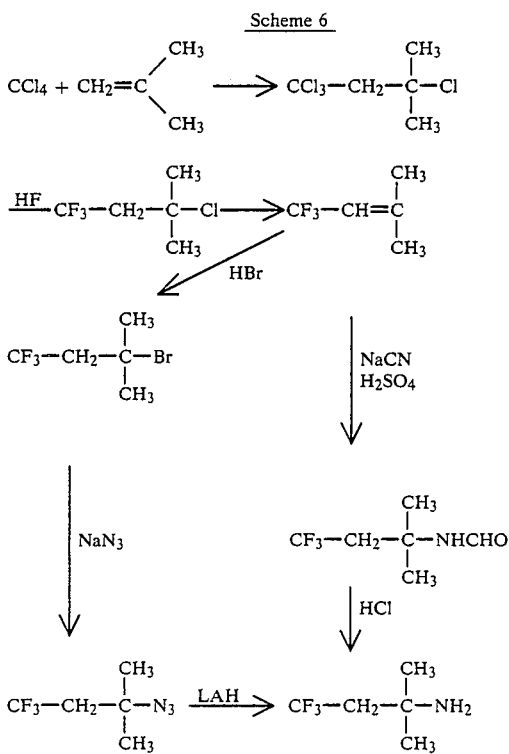

The invention will be more readily understood by reference to the examples which are intended to be illustrative of the invention and not limiting in any manner. All temperatures reported are in degrees Centigrade.

EXAMPLE I

Preparation of 1-cyano-3-(3,3,3-trifluoro-1,1-dimethylpropyl)guanidine

(a) 1,1,1,3-Tetrachloro-3-methylbutane

To a 500 ml Pyrex ampoule fitted with a "rotaflo" tap were added carbon tetrachloride (221 ml, 2.29 mol) and benzoyl peroxide (2.65 g, 10.9 mmol). The ampoule and contents were cooled in liquid nitrogen, and dry isobutene (64.1 g, 1.14 mol) was added in vacuo. The ampoule was sealed and the mixture was allowed to warm to room temperature, then stirred and heated in a water bath at 72°–74° for 63 h to give 1,1,1,3-tetrachloro-3-methylbutane (184.4 g, 0.878 mol, 77%, b.p. 34°–58°/4 mmHg (lit. b.p. about 52°/4 mmHg) which was used without further purification.

(b) 3-Chloro-1,1,1-trifluoro-3-methylbutane

To a 500 ml stainless steel autoclave was added 1,1,1,3-tetrachloro-3-methylbutane (185.0 g, 0.88 mol), then anhydrous hydrogen fluoride (41 ml, 40.6 g, 2.03 mol). The autoclave was sealed, rocked and heated to 130° during 1 h, then maintained at 130° for 5 h to give the product (108.4 g). b.p. 80°–81°.

(c) 1,1,1-Trifluoro-3-methyl-2-butene

To a 500 ml mechanically stirred 4-neck flask was added potassium hydroxide pellets (71.4 g, 1.27 mol) and n-propanol (204 ml). The mixture was stirred and heated to 94° on a water bath to dissolve the solid, then cooled. 3-Chloro-1,1,1-trifluoro-3-methylbutane (125.8 g, 0.784 mol) was added with efficient stirring over 1.3 h. Stirring was continued for 1.5 hrs.

Distillation gave 90.5 g of the olefin shown by g.l.c. (4 m silicone, 35°) to be >99% pure. Redistillation gave 1,1,1-trifluoro-3-methyl-2-butene b.p. 48°–50°. wt.=82.1 g.

(d) 3-Bromo-1,1,1-trifluoro-3-methylbutane

To a 500 ml "Hastelloy" autoclave was added anhydrous ferric chloride (0.78 g) and 1,1,1-trifluoro-3-methyl-2-butene (90.7 g, 0.73 mol), followed by anhydrous hydrogen bromide (89.8 g, 1.11 mol). The autoclave was rocked for 24 h. during which it was warmed from below −88° to room temperature to control the reaction with hydrogen bromide. Distillation gave material (150.2 g.) shown by g.l.c. (2 m silicone, 50° to contain 98% of the required bromo-compound, with only a slight amount of unchanged 1,1,1-trifluoro-3-methyl-2-butene. Redistillation of an aliquot gave a b.p. of 94.5°–95° shown by g.l.c. analysis (2 m silicone, 50°) and i.r. and n.m.r. spectroscopy to be 99% pure 3-bromo-1,1,1-trifluoro-3-methylbutane. wt.=4.06 g.

(e) 3-Azido-1,1,1-trifluoro-3-methylbutane

Sodium azide (54.4 g, 0.837 mol) was dissolved in water (270 ml) in a 1-liter conical flask, and 3-bromo-1,1,1-trifluoro-3-methylbutane (83.0 g, 0.405 mol) and ethanol (225 ml) were added. The mixture was stirred and heated under reflux for 18 h. After 9 h of this period, and again at 17.7 h, by-product 1,1,1-trifluoro-3-methyl-2-butene was allowed to distill from the mixture at a head temperature of 37°→53°. At 18 hours a sample of the reaction mixture contained only a small amount of unchanged 3-bromo-1,1,1-trifluoro-3-methylbutane by g.l.c. analysis (2 m silicone, 50°).

The reaction mixture was distilled at ca. 65 mmHg pressure until 70 g of condensate had been collected; further distillate when examined by g.l.c. (2 m silicone, 50°) contained none of the required azide. The distillate was added to ice water (500 ml), shaken, and the lower organic layer (17.1 g) separated, shaken with an excess of aqueous sodium bicarbonate solution, then with water, and dried ($Na_2SO_4$). The washings were added to the ice-water layer, which was then extracted three times with ether. The combined ether extracts were washed with an excess of aqueous sodium bicarbonate solution, then with water and dried. The ether was removed to leave a residue of the azide concentrate (13.0 g). The azide was not isolated in the pure state, but as a precaution was handled diluted with ether, olefin and unchanged bromo-compound. The separated organic layer (17.1 g, above) by g.l.c. (2 m silicone, 50°) contained 1,1,1-trifluoro-3-methyl-2-butene (27%), 3-bromo-1,1,1-trifluoro-3-methylbutane (17%) and the azide. The product yields estimated by g.l.c. were 3-azide-1,1,1-trifluoro-3-methylbutane (10.0 g, 15%), 1,1,1-trifluoro-3-methyl-2-butene (27.5 g, 55%), and 3-bromo-1,1,1-trifuloro-3-methylbutane unreacted (4.4 g, 5%). The remaining material was partly accounted for as 1,1,1-trifluoro-3-methyl-2-butene in the ether distillate.

When the ether distillate was used for the extraction in a subsequent experiment, a materials balance nearer to 100% was obtained.

(f) 3,3,3-Trifluoro-1,1-dimethylpropylammonium chloride

3-Azido-1,1,1-trifluoro-3-methylbutane (13.7 g, 82.0 mmol), diluted with dry ether (24 ml) was added over 1 h to a stirred suspension of lithium aluminum hydride (6.0 g, 160 mmol) in ether (130 ml) at 14–17°. The mixture was stirred at 20° for 1 hour, cooled to 0° then cold sodium hydroxide (35.0 g) in water (88 ml) was added with vigorous stirring. Steam distillation to a volume of 250–300 ml of distillate removed the amine collected in a flask containing hydrochloric acid (7 ml of 36%) diluted with water (5 ml). The aqueous layer was separated, and the ether layer was shaken twice with a small volume of dilute hydrochloric acid. The combined acidic aqueous extract was evaporated to dryness at 20 mmHg to give a solid residue which was dried then recrystallized from a mixture of isopropanol and petroleum ether 60°–80° to give 3,3,3-trifluoro-1,1-dimethylpropylammonium chloride (9.6 g, 54.1 mmol, 66%), m.p. 214°–215°, pure by IR and NMR spectroscopy. A later experiment gave a crude yield of 79%.

(g) 1-cyano-3-(3,3,3-trifluoro-1,1-dimethylpropyl)guanidine

A mixture of 3,3,3-trifluoro-1,1-dimethylpropylamine hydrochloride (2.67 g, 15 mol), sodium dicyanamide (1.34 g, 15 mmol), and n-butanol (7.5 ml) was sealed in vacuo in a Pyrex ampoule and was heated at 105° for 119 h to give, after solvent removal, a residue (2.87 g) which was crushed and stirred with water (7 ml), then filtered and washed with water, then dried to give a solid (2.57 g) with m.p. 153° (shrinks 145°). The solid was dissolved in methanol (25 ml) then filtered to remove what is presumed to be polymeric dicyanamide (0.06 g). Removal of solvent and drying gave the guanidine (2.35 g) m.p. 153°–4°.

EXAMPLE 2

Preparation of 1-cyano-3-(3,3,3-trifluoro-1-methylpropyl)guanidine (a) 1,1,1-trifluoro-3-iodobutane Trifluoroiodomethane (82.30 g, 0.420 mol) and propene (11.80 g, 0.280 mol) were charged, in vacuo, into a 20-liter photochemical reactor (Hanovia U.V.S. 500). Argon (10 cm pressure) was added and irradiation carried out until the pressure remained constant (48 h). Distillation gave recovered trifluoroiodomethane (26.02 g, 0.133 mol), propene (0.30 g, 0.007 mol), and 1,1,1-trifluoro-3-iodobutane (50.050 g, 0.212 mol, 76%), b.p. 67° at 235 mmHg pure by g.l.c. (2 m D.N.P. at 80°) and I.R. spectroscopy.

(b) 3-Azido-1,1,1-trifluorobutane 1,1,1-Trifluoro-3-iodobutane (20.00 g, 0.084 mol) was added slowly to a stirred solution of sodium azide (13.00 g, 0.200 mol) in aqueous ethanol (60% ethanol, 200 ml) contained in a 500 ml flask (3-necked) with an argon lute, then refluxed for 11 h. The solution was extracted with ether (250 ml), which was washed and dried, and shown by g.l.c. analysis (2 m D.N.P. at 60°) to contain one major product, 3-azido-1,1,1-trifluorobutane, [approximately 9 g (estimated from g.l.c. analysis), 0.059 mol, 70%] which was not isolated because of the explosive hazard.

(c) Reduction of 3-Azido-1,1,1-trifluorobutane

Fresh lithium aluminum hydride (11.00 g, 0.289 mol) was added to dry ether (250 ml) in a 1 liter flask (3-necked) fitted with a stirrer and condenser connected via a cold trap (−76°) to an argon lute. 3-Azido-1,1,1-trifluorobutane [9 g, 0.059 mol (g.l.c. estimated) in 350 ml ether] was added dropwise over 4 h. so that a steady reflux was maintained. The liquid product (ca. 30 ml) which had condensed in the cold trap was returned to the flask and the mixture was refluxed for a further 2 h. The excess of lithium aluminum hydride was destroyed by careful dropwise addition of sodium hydroxide solution (40 g of NaOH in 80 ml of $H_2O$) with vigorous stirring. The liquid was decanted from the solid residue and combined with the liquid product which had again condensed in the cold trap. The solid residue was leached several times with ether and all the combined ether fractions were washed with water (100 ml) and then shaken with 25% hydrochloric acid solution (3×100 ml). The combined water extract was evaporated to give 3,3,3-trifluoro-1-methylpropyl-ammonium chloride [10.0 g, 0.062 mol, 105% based on estimated azide]. m.p. 194°.

(d) 1-Cyano-3-(3,3,3-trifluoro-1-methylpropyl)guanidine 3,3,3-Trifluoro-1-methylpropylammonium chloride (10.3 g, 63 mmol), sodium dicyanamide (5.66 g, 63.6 mmol), and n-butanol were mixed in a 126 ml "Pyrex" ampoule fitted with a "Rotaflo" tap. The tube was heated at 50°→106° (bath) over 4 h., then at 110°–115° (mainly 104–106°) for 60 h. with stirring and periodic shaking. The reaction mixture was transferred with methanol rinse, to a r.b. flask and the solvents were evaporated. The involatile residue was shaken with water (20 ml) and ether (200 ml), filtered, and the aqueous layer was extracted with ether. The ether was dried ($Na_2SO_4$), and distilled on a water bath to 75°. The residue was freed from solvents at 20 mm, then 0.05 mm, heating on a water bath to 100°. The residue (10.58 g) was a viscous liquid, which was shown by i.r. and n.m.r. spectroscopy and elemental analysis to be 1-cyano-3-(3,3,3-trifluoro-1-methylpropyl)guanidine (10.58 g, 54.4 mmol, 87%).

EXAMPLE 3

Use of the Ritter Reaction (a) Preparation of N(3,3,3-Trifluoro-1,1-dimethylpropyl)formamide 1,1,1-Trifluoro-3-methyl-2-butene (16.1 g, 130 mmol), sodim cyanide (6.7 g, 133 mmol), and water (3.1 g) were stirred together in a flask, and cooled in an ice-salt mixture to 1°–6° C. internal temperature. Sulphuric acid (35.3 g of 98%, 353 mmol) was added from a dropping funnel over 45 minutes. After the addition, the cooling bath was removed, and the reaction mixture allowed to warm. A temperature of 35° C. was reached in 12 minutes, and cooling was applied to give 25° C. When the heat of reaction had subsided, the mixture was heated in a water bath to 43° C. during 2 hours and kept at 43° C. for 1.75 hours. The mixture was allowed to cool to 20° C., and the apparatus was then evacuated to 15 mmHg through a −78° C. trap. The mixture was then cooled to 5°–10° C. in a bath of ice and salt, while water (46 ml) was added over 10 minutes from the dropping funnel. The mixture at 25° C. was stirred vigorously and again evacuated to 15 mmHg, to collect unreacted olefin and other volatile products in the −78° C. trap.

The mixture was extracted with ether (3×45 ml) and the combined ether extracts washed with water (30 ml) and dried ($Na_2SO_4$). After distillation of the ether, the residue was distilled in vacuo to obtain a colorless viscous liquid (11.6 g) b.p. 50° C./0.1 1mm which was shown by g.l.c. analysis (1.5 m OV225, 160° C.), i.r., and n.m.r. spectroscopy, and elemental analysis to be N-(3,3,3-trifluoro-1,1-dimethylpropyl)formamaide (11.6 g, 0.69 mmol, 53%).

(b) Preparation of 3,3,3-Trifluoro-1,1-dimethylpropylammonium chloride

To N-(3,3,3-trifluoro-1,1-dimethylpropyl)formamide (5.95 g, 35 mmol) was added hydrochloric acid (118.5 g of 13% w/w, 420 mmol). The mixture was stirred and heated on a water bath. A homogeneous solution was obtained after 7 minutes at 30° C. (bath). They hydrolysis was followed by g.l.c. analysis (1.5 m OV225, 160° C.), and after 5 hours heating at 50°–65° C. (bath) and standing overnight at 20° C., a sample of the reaction mixture was shown to contain less than 1% of the original quantity of the formamide. The aqueous reaction mixture was evaporated at 16–17 mmHg on a water bath at 50°–65° C. The residual solid was dried in a desiccator at 16 mmHg, and shown by m.p., mixed m.p., and i.r. spectroscopy to be 3,3,3-trifluoro-1,1-dimethylpropylammonium chloride (6.11 g, 3.4. mmol, 98%) m.p. 215°–216.5° C. The claimed compound can be formed from the product by reaction of the product with sodium dicyanamide using the technique previously exemplified.

EXAMPLE 4

The Ritter reaction can also be employed to form a formamide from the corresponding alkanol, the formamide being thereafter reduced to the amine from which the ammonium chloride and the claimed compound can be made by techniques previously illustrated.

To illustrate this process embodiment, 4,4-Difluoro-2-methylbutan-2-ol (17.6 g, 0.142 mol), water (4.5 ml), and liquid anhydrous hydrogen cyanide (8.4 ml, 5.8 g, 0.214 mol) previously cooled to 8° C. were added to a 100 ml flask. Sulphuric acid (11.6 ml of 98%≡21.3 g, 0.213 mol) was added dropwise over 1 h, while the mixture was stirred and cooled to 7°–10° C., and the temperature of the mixture was increased to 19° C. over 13 minutes at which temperature the mixture was held for 20 minutes. The mixture was thereafter warmed slowly to 35° C. (some heat of reaction) for 25 minutes and then heated at ca. 50° C. for 3 h.

The mixture was stirred and cooled to 0° C. and water (23 ml) was added. The reaction mixture was then extracted with ether (3×25 ml) and the combined extracts were washed with water (12 ml) and dried ($Na_2SO_4$) overnight. The residual liquid, after removal of the ether, was distilled in vacuo to give N-(3,3-difluoro-1,1-dimethylpropyl)formamide (14.62 g, 68%).

N-(3,3-Difluoro-1,1-dimethylpropyl)formamide (5.0 g, 33.1 mmol), water (42.7 ml), and hydrochloric acid (28.4 ml≡33.5 g of 36%, 0.331 mol) were then magnetically stirred in a 250 ml flask and heated at ca. 60° C. for 4 h. The reaction solution was filtered to separate a small amount of insoluble solid and the filtrate evaporated in vacuo to yield a solid (5.20 g), m.p. 206°–207° C. The solid was recrystallised (isopropanol, 60°–80° C. petroleum ether) to yield 3,3-difluoro-1,1-dimethylpropylammonium chloride. (4.75 g, 29.78 mmol, 90%). The claimed compound is formed from this product using the technique previously identified. The formamide has also been hydrolysed in quantitative yield by standing at 20° for 12 days in solution in one molar methanolic hydrochloric acid used in a 50% excess.

Following is a list of known amines of the formula:

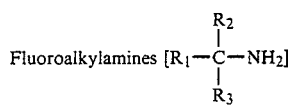

Fluoroalkylamines [$R_1-\overset{R_2}{\underset{R_3}{C}}-NH_2$]

which may be used to prepare corresponding 1-cyano-3-fluoroalkylguanidine derivatives of formula (1).

| $R_1$ | $R_2$ | $R_3$ |
| --- | --- | --- |
| $CF_3CH_2$ | $CH_3$ | $CH_3$ |
| $CF_3CH_2$ | $CH_3$ | H |
| $CF_3CH_2CH_2$ | $CH_3$ | H |
| $CF_3CF_2CH_2$ | $CH_3$ | H |
| $CF_3CH_2$ | H | H |
| $FCH_2$ | $CH_3$ | H |
| $CH_3CH_2$ | $CH_2F$ | H |
| $C_3H_7CF_2$ | $C_3H_7$ | H |
| $C_3F_7CH_2$ | $C_2H_5$ | H |
| $CF_3CH_2CH_2$ | $CF_3$ | H |
| $CH_2=CHCH_2$ | $CH_2F$ | H |
| $CH_3$ | $CF_3$ | $CH_3$ |
| $CH_3$ | $CF_3$ | H |
| $C_2H_5$ | $CF_3$ | H |
| $F_2CHCH_2$ | $CH_3$ | $CH_3$ |
| $C_3H_7$ | $CF_3$ | H |
| $C_4H_9$ | $CF_3$ | H |
| $i-C_3H_7$ | $CF_3$ | H |
| $CH_3-CH(CH_3)-CH_2$ | $CF_3$ | H |

Pharmacology Data

Spontaneously Hypertensive Rat (SHR)

Arterial systolic blood pressure was measured in warmed rats (rats were kept at 35°–37° C. before measurement) with an indirect tail cuff method. Pre-treatment pressures were obtained either on the day before or the morning of the experiment. Only rats with a systolic pressure of 180 mmHg or higher were used. The animals were randomly distributed into groups of five (5) and received vehicle or test compound orally. A 4% solution of Instant Clearjel prepared in distilled water served as the vehicle, and the animals received vehicle or test compound of the Example indicated in a volume equal to 1% of their body weight. The results are given in Table 1.

TABLE 1

| | Acute studies at 75 mg/kg (p.o.) | | | |
| --- | --- | --- | --- | --- |
| | Percent reduction in B.P. at ( ) Hrs.post dose | | | |
| Example No. | % Δ @ 2hrs. | % Δ @ 5 hrs. | % Δ @ 7.5 hrs. | % Δ @ 24 hrs. |
| 1 | 43 | 49 | 42 | 45 |
| 2 | 23 | 18 | 15 | — |
| Guancydine | 48 | 48 | 47 | 12 |

Dopaminergic activity

Groups of ten mice are dosed intraperitoneally with the drug of Example 1 and thirty minutes later they are given orally LON 954 (50 mg/Kg), a dopamine antagonist which induces tremors symptomatic of Parkinson's disease. The mice are then observed for protection against tremors. The results are given in Table 2.

TABLE 2

| Dose (i.p., mg/Kg) | No. of mice protected |
| --- | --- |
| 25 | 2/10 |
| 50 | 7/10 |

It is postulated that, for use as an anti-hypertensive agents, the method of administering the related compounds of the present invention is substantially identical to methods established for the hydrocarbon analogue 1-t-amyl-3-cyanoguanidine, e.g. preferably by oral administration. It may be orally administered, for example, with an inert diluent or with an assimilable edible carrier, or enclosed in hard or soft gelatin capsules, or compressed into tablets, or incorporated directly with the food of the diet.

The amount of a single dose or of a daily dose to be given will vary, but should be such as to give a proportionate dosage of from about 1 mg. to about 15 mg. per kg. of body weight per day. In terms of total weight of active ingredient, this is usually from about 0.1 g. to about 1.0 g. per daily dosage. This dosage regimen may be adjusted to provide the optimum therapeutic response; for example, several divided doses may be administered daily or the dose may be proportionately reduced as indicated by the exigencies of the therapeutic situation.

For therapeutic administration, the active compound of this invention may be incorporated with excipients and used, for example, in the form of tablets, troches, capsules, elixirs, suspensions, syrups, wafers, chewing gum and the like. Such preparations should contain at least 0.1% of active compound. The percentage in the preparations may, of course, be varied and may conveniently be between about 5% to about 75% or more of the weight of the unit. The amount of active compound in such therapeutically useful preparations is such that a suitable dosage will be obtained. Preferred preparations according to the present invention are prepared so that a dosage unit form contains between about 10 and 200 milligrams of active compound.

The tablets, troches, pills, capsules and the like may contain the following: a binder such as gum tragacanth, acacia, corn starch, or gelatin; a disintegrating agent such as a corn starch or potatoe starch, alginic acid and the like; a lubricant such as magnesium stearate; and a sweetening agent such as sucrose or saccarin may be added or a flavoring agent such as peppermint, oil of wintergreen or cherry flavoring. A syrup or elixir may contain the active compounds, sucrose as a sweeting agent, methyl and propyl parabens as preservatives, a dye and a flavoring such as cherry or orange flavor.

Many equivalent modifications of the present invention will be apparent to those skilled in the art without a departure from the inventive concept.

What is claimed is:

1. The compound

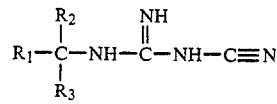

in which $R_1$, $R_2$ and $R_3$ are the same or different members of the class of hydrogen, fluorine, lower fluoroalkyl or lower alkyl or lower alkenyl provided that at least one member is fluorine or lower fluoroalkyl.

2. The compound of claim 1 wherein $R_1$ if fluoroalkyl and $R_2$ and $R_3$ are the same or different members of the class of hydrogen and methyl.

3. The compound of claim 2 wherein $R_1$ is $CF_3\text{—}CH_2$.

4. The compound of claim 3 wherein $R_2$ is hydrogen and $R_3$ is methyl.

5. The compound of claim 3 wherein $R_2$ and $R_3$ are methyl.

6. A therapeutic composition in oral dosage unit form useful for lowering elevated blood pressure comprising from 0.1 gram to 1.0 grams per daily dosage unit of a compound of the formula of claim 5 in association with an acceptable pharmaceutical carrier.

7. The method of lowering elevated blood pressure which comprises administering orally to a mammal an amount ranging from 1 mg. to 15 mg. per kilogram of body weight per day of a compound of the formula of claim 5.

* * * * *